United States Patent [19]

Liotta et al.

[11] 4,028,358

[45] June 7, 1977

[54] 6-FLUORO-9-PERFLUOROBUTYL PURINE

[76] Inventors: Charles L. Liotta, 3691 Stanford Circle, Decatur, Ga. 30034; John D. Muzzy, 631 Norfleet Road NW., Atlanta, Ga. 30305

[22] Filed: Sept. 4, 1973

[21] Appl. No.: 393,718

[52] U.S. Cl. .................................. 260/254; 32/15; 106/35; 260/252

[51] Int. Cl.$^2$ ...................................... C07D 473/40

[58] Field of Search ........................... 260/252, 254

[56] References Cited

UNITED STATES PATENTS

| 3,274,193 | 9/1966 | Horwitz et al. | 260/254 |
|---|---|---|---|
| 3,310,561 | 3/1967 | Bader | 260/252 |
| 3,664,991 | 5/1972 | Kaye | 260/252 |

OTHER PUBLICATIONS

Barlin et al., *J. Chem. Soc.*, Perkin Trans. I (G.B.) No. 9–10, pp. 1269–1272.
Pitha et al., *J. Org. Chem.*, vol. 33 pp. 1341–1344 (1968).

*Primary Examiner*—Paul M. Coughlan, Jr.
*Attorney, Agent, or Firm*—Jones, Thomas & Askew

[57] ABSTRACT

Novel purine compounds substituted with either fluorine or trimethylammonium are useful as adhesives or continuous and non-continuous coatings and are prepared by a novel process.

1 Claim, No Drawings

6-FLUORO-9-PERFLUOROBUTYL PURINE

This invention relates to the preparation of novel purine compounds and the use of these compounds to alter the physical and chemical properties of solid, nucleophilic surfaces through bimolecular, nucleophilic displacement reactions. More particularly, this invention is directed to the use of novel purine compounds as dental adhesives or dental coatings.

The adherence of a material of one composition to a material of a totally different composition has always been difficult because of the differences in physical and chemical properties at the surfaces of the two materials. For example, metal and glass are difficult to adhere to one another, as are wood and glass, plastic and metal, and leather and plastic. A particular area in which adherence of unlike materials to each other is both tremendously important and equally troublesome is the dental field. New methods and adhesives are continuously being developed to overcome the problems encountered in adhering restoration materials and other materials such as orthodontic plastic brackets to the tooth structure.

Many types of methods and adhesives have been used in order to provide adhesion between the tooth structure and other materials. Nearly all of these methods and adhesives have to some extent resulted in mechanical interlocking between the adhesive and the tooth structure. For example, in preparing a restoration, the dentist undercuts the cavity to leave some of the tooth surface overlapping the drilled out area in order to mechanically prevent the restoration from falling out. Recently, mechanical interlocking has been enhanced by etching the tooth surface with dilute acids which selectively etch the enamel and dentin to provide for interlocking of the adhesive and tooth structure on a microscopic scale.

Specific adhesives which have been used to provide mechanical adhesion of various materials to the tooth structure include both the inorganic salts such as zinc phosphate, zinc oxide-eugenol, and certain silicates and the organic polymers such as methacrylates, cyanoacrylates, and urethanes. The polymeric adhesives are normally formed by in situ polymerization reactions on the tooth surface. Disadvantages of polymeric adhesives are that the adhesives have a high coefficient of thermal expansion and also shrink when polymerized. Disadvantages attendant to both inorganic salt adhesives and polymeric adhesives are lack of color stability, weak adhesive bonds, and tendency to break down from attack by the various chemicals and organisms normally within the mouth.

A recent innovation in dental adhesion has been the use of surface active coupling agents such as the organo-silanes and the addition-reaction product of N-phenylglycine and glycidyl methacrylate that react with the tooth structure. The organo-silanes have two types of functional groups, one of which reacts with the bulk adhesive, such as a vinyl group, and another of which reacts with the tooth structure, such as a silanol group. The disadvantage of using the known adhesives of this type is the the water or the other chemicals normally present in the mouth tend to reverse the reaction which produces the adhesive bond. As an example, a silanol group reacts with the hydroxyapatite within the tooth structure, creating a strong adhesive bond, and during the reaction water is given off as a by-product. The water given off, in addition to the water already present in the mouth, tends to reverse the reaction and to prevent the adhesive bond from being formed. Similar detrimental reversible reactions occur when the adhesive agent contains either a N-phenylglycine group or a carboxylic acid group.

It is, therefore, an object of the present invention to provide novel purine compounds which are capable of reacting with both the tooth structure and materials to be adhered to the tooth structure to form a strong adhesive bond which is not weakened or destroyed by the water or the other chemicals normally found within the mouth.

It is another object of the present invention to provide novel purine compounds which are capable of reacting with the tooth structure to provide a protective coating which is not weakened or destroyed by the water or the other chemicals normally found within the mouth.

In accordance with the present invention, there is provided a novel class of purine compounds respresented by the following formula:

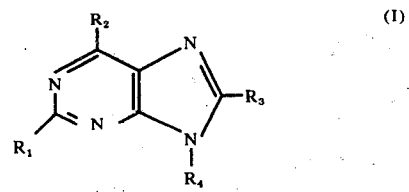

wherein:
$R_1$, $R_2$, $R_3$ are either hydrogen, fluorine, or trimethylammonium with at least one of $R_1$, $R_2$ and $R_3$ being either fluorine or trimethylammonium;

$R_4$ is either an organic reactive substituent capable of undergoing either a free radical, ionic, ring-opening, or condensation copolymerization reaction, or an organic non-reactive substituent such as alkyl, perfluoroalkyl or alkyl ether.

Preferably, only one of $R_1$, $R_2$, and $R_3$ is either fluorine or trimethylammonium with the remaining two groups being hydrogen. Most preferably, $R_1$ and $R_3$ are hydrogen and $R_2$ is fluorine.

When $R_4$ is an organic reactive substituent capable of undergoing a copolymerization reaction, $R_4$ should contain a functional component, such as amino, vinyl, epoxy, methacryloxy, or mercapto, which contributes to the copolymerization reaction. Preferred $R_4$ reactive substituents are ethylene acrylate, methylene acrylate, β-(aminoethyl)-γ-aminopropyl, γ-aminopropyl, β-(3,4-epoxycyclohexyl)ethyl, 2,3-epoxypropyl, γ-glycidoxypropyl, γ-methacryloxypropyl, and γ-mercaptopropyl, with γ-methacryloxypropyl being the most preferred.

Suitable $R_4$ non-reactive substituents are the alkyls, such as methyl, ethyl, propyl, and the like, the perfluoroalkyls, such as perfluoromethyl, perfluoroethyl, perfluoropropyl, and the like, and the alkyl ethers such as methoxymethyl, ethoxymethyl, and the like. The most preferred alkyl, perfluoroalkyl, and alkyl ethers are methyl, perfluorobutyl, and methoxymethyl, respectively.

When the novel purine compounds of the present invention are reacted with the tooth structure, the fluorine of trimethylammonium group present on the ring at the $R_1$, $R_2$ or $R_3$ position is displaced by a nucleophilic reactive group within the tooth structure to form a covalent bond between the tooth structure and the purine compound. Suitable nucleophilic reactive groups are —OH, —S—, —NH$_2$, —SH and —COO$^-$ and such groups are present in the tooth structure within hydroxyapatite and peptide moieties such as histidine, hydroxylysine, lysine, arginine, methionine, and the like. The covalent bond formed by the nucleophilic displacement reaction is very strong and is not subject to break-down either by the reaction being reversed by water and other chemicals normally present in the mouth or by direct chemical attack by the organisms and chemicals present in the mouth. In addition, the presence of the purine compound on the tooth structure is not harmful to the tooth and does not shorten its life. Exemplary of the possible reactions which could occur between 6-fluoro-9-methoxymethylpurine, one of the novel purine compounds of the present invention, and the tooth structure are:

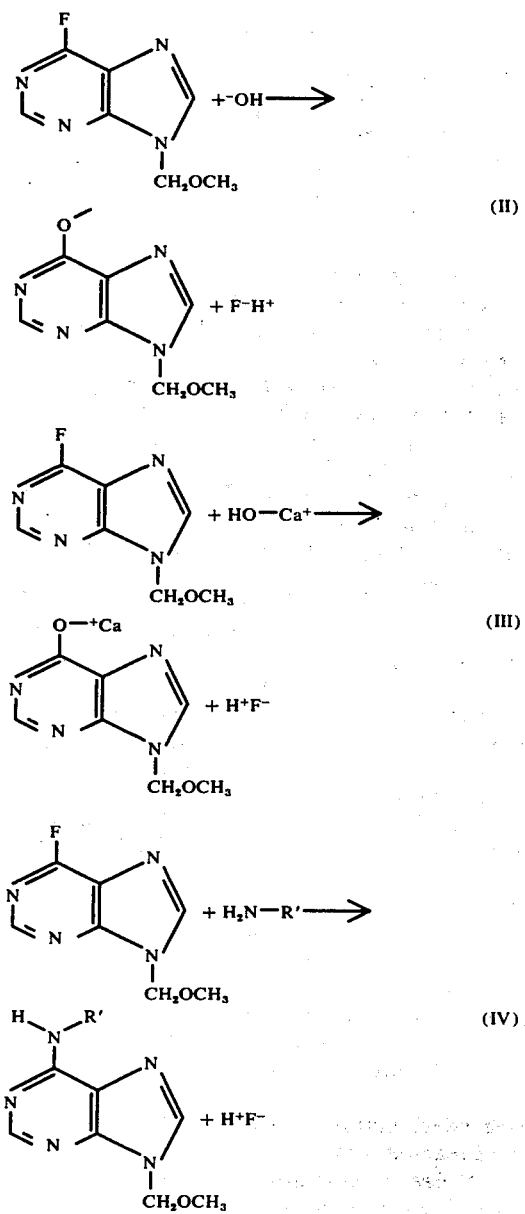

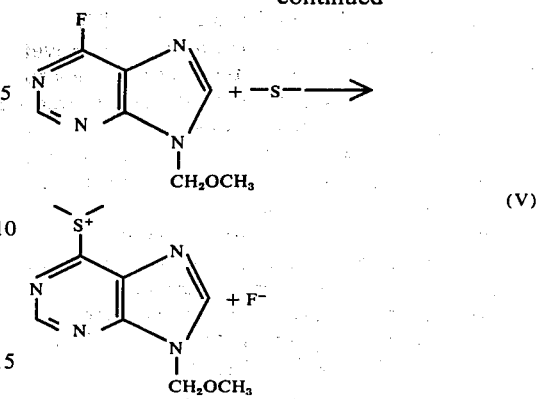

The reactions depicted in II, IV and V above represent possible reactions between the 6-fluoro-9-methoxymethylpurine and either the histidine, hydroxylysine, lysine, arginine, or methionine present within the tooth structure. The reaction depicted in III above represents the possible reaction between the 6-fluoro-9-methoxymethylpurine and the hydroxyapatite present within the tooth structure. In each of the reactions depicted, fluorine is displaced from the ring by a nucleophilic reactive group. The displaced fluorine thus becomes available to harden the tooth structure in the vicinity of the reaction site as is a customary practice in dentistry today.

It is to be understood that many other reactions between the novel purine compounds of the present invention and the tooth structure are possible depending upon the number and position of the fluorine and trimethylammonium groups on the aromatic ring.

The R$_4$ substituent at the 9-position on the aromatic ring of the novel purine compounds is selected in accordance with whether an additional material is to be adhered to the tooth structure or whether the purine compounds are to be used as a protective coating for the tooth structure. When an additional material is to be adhered to the tooth structure, the R$_4$ substituent is selected so that a suitable polymerization reaction can be obtained between the additional material and the purine compounds.

If the material to be adhered to the tooth structure is either an alkene, substituted alkene, diene, methacrylate or a similar unsaturated compound, the a R$_4$ substituent is selected that is capable of undergoing a free radical or ionic polymerization reaction with these compounds. Suitable R$_4$ substituents for reactions involving free radical or ionic polymerization are the vinyl, $\gamma$-methacryloxypropyl and $\gamma$-mercaptopropyl groups.

If the material to be adhered to the tooth structure is either a carboxylic acid or an amine, then a R$_4$ substituent is selected that is capable of undergoing either a condensation or ring-opening polymerization reaction with either a carboxylic acid or the amine. Suitable R$_4$ substituents for reactions with the carboxylic acid in either a condensation or ring-opening polymerization reaction are the $\beta$-(aminoethyl)-$\gamma$-aminopropyl and $\gamma$-aminopropyl groups. Suitable R$_4$ substituents for reactions with the amine in either a condensation or ring-opening reaction are the $\beta$-(3,4-epoxycyclohexyl)ethyl and $\gamma$-glycidoxypropyl groups.

When the purine compounds are to be used as a protective coating for the tooth structure, the R$_4$ substituent is selected so that suitable characteristics are obtained at the tooth surface. The preferred $R_4$ substituents for the purine compounds to be used as a protective coating are the perfluoroalkyls and the most preferred perfluoroalkyl is the perfluorobutyl. The perfluorobutyl, although non-reactive towards the water and other chemicals present in the mouth, aids in protecting the tooth structure.

Specific uses for the novel purine compounds of the present invention with $R_4$ reactive substituents include the adhesion of restoration materials and pit and fissure sealants to tooth structure as well as the adhesion of bone cements to bone. In each application a fluoropurine compound containing a methacryloxypropyl group is applied from solution to the cavity, tooth surface, or bone surface. The purine reacts with nucleophilic centers on the surfaces by displacement of fluorine, forming a covalent bond with these nucleophilic centers. Following this surface reaction, a cavity restorative resin, pit and fissure sealant, or bone cement containing acryloxy moieties is applied to be treated surface and copolymerized with the methacryloxypropyl group on the purine ring by a free radical reaction. In each case the restorative resin, pit and fissure sealant, or bone cement is covalently bonded through the purine to the tooth cavity, dental surface, or bone surface, respectively.

A specific use in the field of dentistry for the purine compounds of the present invention with $R_4$ non-reactive substituents is the prevention of plaque build-up on the tooth structure. By reacting with the tooth structure and occupying the space adjacent to the tooth structure, the purine compounds effectively eliminate any reaction sites for the plaque. Hence, no plaque build-up can occur at these reaction sites.

One method of preparing the novel purine compounds in accordance with the present invention involves the initial step of reacting a commercially available purine compound having groups substituted at the 6- and 9- positions with trimetylamine to obtain an intermediate purine compound. This intermediate purine compound is then reacted with a fluoride salt, such as LiF, NaF, KF, or CsF, using a sterically hindered alcohol to obtain the novel purine compounds. These two steps are exemplified in the following two reactions in which the final purine compound is 6-fluoro-9-methoxymethylpurine:

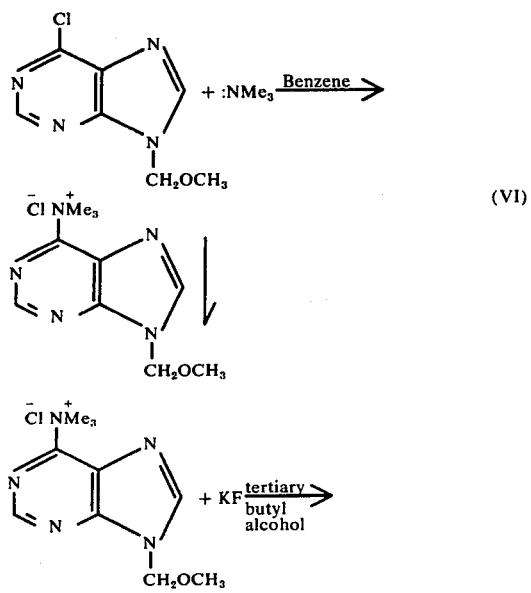

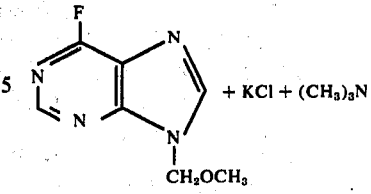

Another method of preparing the novel purine compounds involves initially solubilizing potassium fluoride in either a non-polar, aprotic media or a polar, aprotic media by complexing the potassium ion in either a polyoxa- or polyaza- crown ether dissolved in that media. The crown ether must have a cavity diameter capable of accommodating the potassium ion. Then, the solubilized potassium fluoride is reacted with a commercially available chloropurine to form the novel fluoropurine.

The following illustrative examples are presented in an effort to further describe the present invention.

EXAMPLE 1

Preparation of 6-fluoro-methoxymethylpurine

Step 1. A 500 ml. round bottom flask equipped with a magnetic stirrer was charged with 300 ml. benzene and 4.20 g of 6-chloro-9-methoxymethylpurine. The purine went into solution immediately. Two 25 ml. portions of trimethylamine were then added rapidly to the mixture, and a white crystalline precipitate of 6-trimethylammonium-9-methoxymethylpurine chloride began to form in the solution immediately. The flask was stoppered and the mixture was allowed to react for 10 hours with constant stirring.

At the end of 10 hours, the reaction mixture was filtered through a coarse sintered glass filter and the white precipitate remaining on the filter was washed with two 20 ml. portions of dry benzene. The white precipitate was then dried in a drying vessel under vacuum for 12 hours. A yield of 4.86 g, or 89.2% based on moles of 6-chloro-9-methoxymethylpurine, of 6-trimethylammonium-9-methoxymethylpurine chloride was obtained.

Step 2. A 1,000 ml. round bottom flask equipped with a magnetic stirrer and a $CaCl_2$ drying tube was charged with 500 ml. of tertiary butyl alcohol and 1.563 g of potassium fluloride. Then, 1,504 g of 6-trimethylammonium-9-methoxymethylpurine chloride was added to the mixture. The compounds were allowed to react for 12 hours. The progress of the reaction was checked by quenching 2–3 drops of the reaction mixture in 5–10 ml. of distilled water and scanning the sample with the UV spectrum. Initially, the only peak visible was at 264 nm. As the reaction proceeded a peak at 248 nm became visible and indicated the presence of 6-fluoro-9-methoxymethylpurine.

At the end of 12 hours, the reaction mixture was filtered through a coarse sintered glass filter and the 6-fluoro-9-methoxymethylpurine remaining on the filter was dried under a vacuum. Thereafter, the 6-fluoro-9-methoxymethylpurine was recrystallized from hexane and a yield of 0.760 g was obtained. This yield was 61.7% based on moles of 6-chloro-9-methoxymethylpurine which was originally used.

EXAMPLE 2

Preparation of 6-fluoro-9-methoxymethylpurine

To 10 ml of a solution of 0.25 M 1, 4, 7, 10, 13, 16-hexaoxacyclooctadecane in acetonitrile there was added 2.5 g of anhydrous potassium fluoride. The mixture was stirred at room temperature for 1 hour. Four grams of 6-chloro-9-methoxymethylenepurine were then added to the mixture and the resulting reaction mixture was stirred at room temperature for 2 days. At the end of this time the reaction mixture was filtered and the acetonitrile was evaporated from the solid remaining on the filter. The solid was analyzed and identified at 6-fluoro-9-methoxymethylpurine. It was determined that the reaction gave a quantitative yield of purine compound of 100%.

EXAMPLE 3

Preparation of dentin collagen

A large Bovine molar tooth was preserved in Normal Saline solution immediately after extraction. The tooth was refrigerated in the solution at 10° C. to retard degradation. The tooth was sectioned at the enamel cementum junction with an Exacto hand saw. The pulp and residual soft tissues were removed. Both sections of the tooth were immersed in 100 ml of a 15% solution of disodium ethylenediamine tetraacetic acid ($Na_2EDTA$) in deionized water neutralized to pH 7.1 with normal sodium hydroxide solution. The treatment was continued at 37° C. until constant weight was achieved after five days. A 45% weight loss was observed after 4 days in the neutral EDTA. At this point the dentin separated from the enamel due to shrinkage. The enamel was easily removed and discarded with dental tool. The dentin was soft like a sponge and contained considerable entrained water. The dentin derived material was washed with neutral deionized water. This material was defined dentin collagen without drying to maintain its structure.

EXAMPLE 4

To 0.7076 g of dentin collagen prepared according to Example 3 there was added a solution made by dissolving 0.009 g of 6-fluoro-9-methoxymethylpurine in 10 ml. of water. The resultant mixture was allowed to react for 20 hours at 50° C. The water was then evaporated under vacuum and the dried residue was washed with deionized water to remove any unreacted 6-fluoro-9-methoxymethylpurine. The washed residue was hydrolyzed by refluxing in 120 ml. of 1N HCl for 3 hours. The resulting solution was filtered and analyzed by spectrophotometric techniques. The UV analysis indicated the presence of the purine nucleus thus providing evidence that the 6-fluoro-9-methoxymethylpurine reacted with the dentin collagen.

EXAMPLE 5

A tooth crown from a recently extracted bovine tooth was crushed under deionized water to yield 1.6640 g of material. The crushed tooth was treated in a Rotovap with 0.0090 g of 6-fluoro-9-methoxymethylpurine in 10 ml. of deionized water (pH 7.0) for 20 hours at 50° C. Afterwards, the water was evaporated under vacuum and the residue was washed with deionized water to remove any unreacted 6-fluoro-9-methoxymethylpurine. The residue was then hydrolyzed with 60 ml of 1N HCl over a 3-hour period. The resultant solution was filtered and subjected to UV analysis. Evidence was obtained as in Example 4 that the 6-fluoro-9-methoxymethylpurine had reacted with the crushed tooth.

EXAMPLE 6

To a standard 1 cm U.V. cell was added 2.75 ml. of a $1.097 \times 10^{-4}$ M solution of 6-fluoro-9-methoxymethylpurine in water (E=6.180 in water at 25° C, max=247-min). The absorption at this concentration was A=0.678. A stream of dry nitrogen gas was applied over the solution until the water had evaporated. Immediately thereafter, 0.0094 g. of hydroxyapatite and 0.25 ml. of absolute ethanol were added to the cell. The resultant mixture was allowed to react for 3 hours with occasional shaking. Then, the ethanol was evaporated with a stream of dry nitrogen gas directed over the mixture. To the remaining solid material in the cell was added 2.75 ml. of distilled water, and the resultant mixture was shaken and centrifuged to settle the hydroxyapatite on the bottom of the cell. The U.V. absorption of the solution was determined to be A=0.380, corresponding to a concentration of $0.614 \times 10^{-4}$ M in 6-fluoro-9-methoxymethylpurine. The percent reaction was 44%.

Other uses for which the novel purine compounds of the present invention are suitable include various cements for bone, living tissue, plastics, and wood and as a release agent for continuous and non-continuous coatings.

While this invention has been described in detail with particular reference to preferred embodiments thereof, it will be understood that variations and modifications can be effected within the spirit and scope of the invention as described hereinbefore and as defined in the appended claims.

We claim:

1. A purine compound of the following formula:

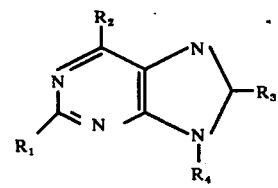

wherein $R_1$ and $R_3$ are hydrogen, $R_2$ is fluorine, and $R_4$ is perfluorbutyl.

* * * * *